United States Patent [19]

Heider et al.

[11] Patent Number: 5,395,960
[45] Date of Patent: Mar. 7, 1995

[54] PREPARATION OF VINYL CARBOXYLATES

[75] Inventors: Marc Heider, Neustadt; Thomas Ruehl, Frankenthal; Jochem Henkelmann, Mannheim, all of Germany

[73] Assignee: BASF Aktiengesellschaft, Ludwigshafen, Germany

[21] Appl. No.: 234,383

[22] Filed: Apr. 28, 1994

[30] Foreign Application Priority Data

Apr. 28, 1993 [DE] Germany ............... 43 13 922.1

[51] Int. Cl.⁶ .................. C07C 69/01; C07C 67/04
[52] U.S. Cl. .................................... 560/242; 560/241
[58] Field of Search .............................. 560/242

[56] References Cited

U.S. PATENT DOCUMENTS 3,607,915  9/1971  Borsboom et al. ............ 560/242
4,145,486  3/1979  Haag et al. ................... 521/31

FOREIGN PATENT DOCUMENTS 0512656  11/1992  European Pat. Off. .

OTHER PUBLICATIONS

Organometallics, vol. 2, No. 11, pp. 1689–1690, M. Rotem, et al., "Addition of Carboxylic Acids to Alkynes Catalyzed by Ruthenium Complexes, Vinyl Ester Formation"–Mar. 1983.

J. Org. Chem., vol. 52, pp. 2230–2239, Take-aki Mitsudo, et al., "Ruthenium-Catalyzed Selective Addition of Carboxylic Acids to Alkynes, a Novel Synthesis of Enol Esters"–Nov. 6, 1986.

Primary Examiner—Arthur C. Prescott
Attorney, Agent, or Firm—Oblon, Spivak, McClelland, Maier & Neustadt

[57] ABSTRACT

Preparation of vinyl carboxylates by the reaction of a carboxylic acid with acetylene in the presence of a platinum metal complex catalyst, which contains as ligands carbon monoxide or a nitrile (I), a tertiary nitrogen base (II), a tertiary phosphorus compound (III) having C-organic and/or O-organic radicals or mixtures of said compounds.

The end products serve as monomers or comonomers for polymer dispersions.

8 Claims, No Drawings

PREPARATION OF VINYL CARBOXYLATES

The present invention relates to an improved process for the preparation of vinyl carboxylates by the reaction of a carboxylic acid with acetylene in the presence of a platinum metal complex catalyst.

EP-A 512,656 describes a process for the vinylation of Brönsted acids, including carboxylic acids, with acetylene, in which ruthenium metal on an inert support functions as heterogeneous catalyst. However, the use of heterogeneous catalysts causes chemical engineering problems if the catalyst is not disposed in a fixed bed, through which the mixture of the materials used flows. Fixed bed catalysis is however only economical in large-scale processes and is usually designed only for the preparation of a certain product. If it is desired to alternately prepare different products in a single plant, homogeneous catalysis is more suitable.

Furthermore, the reaction of carboxylic acids with alkynes to produce the corresponding alkenyl esters is known from the research work of Mitsudo et al (J. Org. Chem. 52, page 2230, [1987]) with the aid of cyclooctadienyl-ruthenium complexes acting as catalysts, in which maleic anhydride and tertiary phosphines function as further ligands. Apart from the fact that these complexes are difficult to obtain and are scarcely suitable for reactions on an industrial scale, they require in the case of acetylene disproportionately long reaction times. According to this paper, no reaction whatever takes place when the attempt is made to react methacrylic acid with pent-1-yne in the presence of a ruthenium complex and tributyl phosphine as the only ligands.

In *Organometallics* 2, page 1689, [1983], a report has been written by Rotem et al on the reaction of carboxylic acids with alkynes in the presence of ruthenium carbonyl complexes or ruthenium carbonyl acetate complexes. But here only substituted alkynes were caused to undergo reaction, not acetylene itself.

Thus it is an object of the present invention to provide an improved and universal process for the vinylation of carboxylic acids.

Accordingly, we have found a process for the preparation of vinyl carboxylates by the reaction of a carboxylic acid with acetylene in the presence of a platinum metal complex catalyst, wherein a complex of a platinum metal is used as platinum metal complex catalyst, which contains, as ligands, carbon monoxide, a monovalent or polyvalent nitrile (I), a monovalent or polyvalent nitrogen base (II), a monovalent or polyvalent tertiary phosphorus compound (III) having C-organic and/or O-organic radicals, or mixtures of said compounds.

The catalysts used in the process of the invention are complex compounds of the platinum metals ruthenium, rhodium, palladium, osmium, iridium, or platinum, of which ruthenium is especially preferred.

Complexes having one or more metal nuclei are suitable catalysts, which either have metal-metal bonds, or in which the metal atoms are linked by ligands.

The metals in the complexes can be of zero valence, or are present in a positive or negative oxidation stage, and the coordination sites of the platinum metal may be completely or partially occupied by the ligands.

Such ligands are carbon monoxide, the monovalent or polyvalent nitriles I, tertiary amines II as well as tertiary phosphorus compounds (III) having C-organic and/or O-organic radicals. Characteristic of these ligands is the fact that they are capable of undergoing chelation with the platinum metal on account of their electron pair on the C atom of the carbon monoxide, and on the N atom or P atoms of the ligands I to III as defined above, respectively.

Monovalent or polyvalent nitriles to be used in the invention can be represented by the general formula I

in which R stands for a C-organic radical, and preferably for a $C_1$-$C_{18}$ alkyl group, primarily a $C_1$-$C_4$ alkyl group such as the methyl, ethyl, n-propyl and n-butyl groups, a cycloalkyl group having from 5 to 7 ring members, primarily the cyclopentyl and cyclohexyl groups, an aryl group, such as the naphthyl and phenyl groups, primarily the phenyl group, an aralkyl group and preferably one having an unbranched alkyl chain, such as the benzyl group or the 2-phenylethyl group.

Acetonitrile, propionitrile, benzonitrile, and benzyl nitrile are examples of suitable nitriles.

Of the monovalent or polyvalent tertiary nitrogen bases, tertiary amines of the formula IIa

are particularly suitable, in which the radicals R denote the same or different C-organic groups, which may be interconnected. The same applies to the preferred radicals R as stated above with respect to the radicals of the nitriles (I).

Generally speaking, those tertiary nitrogen bases II are preferred, whose radicals R have in all not more than 20 C atoms. Also preferred are those compounds II which have three identical radicals, or carry two identical $C_1$-$C_4$ radicals and one $C_5$-$C_{18}$ radical.

Trimethylamine, triethylamine, N,N-dimethylethylamine, tri-n-propylamine, tri-n-butylamine, N,N-dimethyl-n-octylamine, N,N-dimethylcyclohexylamine, 1-methylpyrrolidine, N,N-dimethylbenzylamine, N,N-diethylaniline, triphenylamine, and dimethylstearylamine are examples of particularly suitable amines IIa.

Hetero-aromatic nitrogen bases (IIb) are also suitable as ligands, examples being pyridine, 2,2'-bipyridyl, pyrimidine, unsubstituted triazines, quinoline, isoquinoline, 1,10-phenanthroline, poly(2-vinylpyrrolidone), and purine and preferably pyridine, 2,2'-bipyridyl, 1,10-phenanthroline, and poly(2-vinyl pyridine).

The monovalent or polyvalent tertiary phosphorus compounds having C-organic and/or O-organic radicals can be represented by the general formel III

in which the groups R are the same or different and of a C-organic or O-organic nature.

The variables m and r can assume the values 0 or 1. Thus the respective compounds are phosphines (m, n, r=0), phosphinites (one variable=1), phosphonites (two variables=1) or phosphites (m, n, r=1).

The suitable and preferred radicals R have the same meanings as in the case of the nitriles (I).

Tertiary phosphines III having identical radicals R are preferred due to their ease of preparation.

Triethyl phosphine, tri-n-propyl phosphine, tri-n-butyl phosphine, tricyclohexyl phosphine, tribenzyl phosphine, triphenyl phosphine, trimethyl phosphite, triethyl phosphite, tri-n-propyl phosphite, tri-isopropyl phosphite, tri-n-butyl phosphite, tribenzyl phosphite, and triphenyl phosphite are examples of suitable tertiary phosphorus compounds III.

The nature of the radicals R is not, as far as has been observed, of basic importance for the nitriles I, the tertiary amines IIa, and tertiary phosphorus compounds III, i.e. all complexes of a specific metal have the desired activity within the usual range of variation of the degree of activity.

For economical reasons, compounds are preferred which have simple radicals R. Such simple radicals are predominantly the methyl, ethyl, n-propyl, isopropyl, n-butyl, and phenyl groups.

The radicals R can in all cases be unsubstituted hydrocarbon radicals, or radicals carrying inert substituents such as alkoxy, aryloxy, halogen, alkoxycarbonyl, oder nitrile groups. Nitrile groups and radicals having a tertiary nitrogen atom or tertiary phosphorus atom are of particular significance as substituents. Such suitable ligands are for example N,N,N',N'-tetramethylethylenediamine, 1,2-bis(dimethylphosphino)ethane, or o-phthalodinitrile. Thus in these cases the ligands are such as have a number of coordination sites.

Of these polyfunctional ligands, ligands having a polymeric basic framework are also significant. Such polymeric ligands are known per se or can be obtained by conventional methods (cf, e.g., U.S. Pat. No. 4,145,486).

Polymers such as contain only identical chelatable groups are preferred due to the greater ease with which they can be prepared, examples being polyacrylonitrile, poly(4-vinylpyridine), and poly(diphenylphosphinostyrene).

In a preferred embodiment of the process of the invention, the catalysts can be produced in situ during the reaction, if a salt of a platinum metal and the chelating agents of the invention are added as such to the reaction mixture.

In the synthesis of the catalysts, the chelating agent is added to the platinum metal compounds preferably in an amount of up to four times the stoichiometric amount.

Compounds of platinum metals suitable for this in situ production of the catalyst are preferably the chlorides, nitrates, acetates, and acetylacetonates. The chlorides are particularly preferred.

$PdCl_2$, $Pd(OAc)_2$, and $RuCl_3 \cdot xH_2O$ (Ru content from 40 to 43 wt %), $Ru(acac)_3$, $OsCl_3$, and $RhCl_3$ are examples of suitable salts.

The amount of catalyst used is generally from 0.1 to 10 and preferably from 0.5 to 5 mol % of the amount of the carboxyl groups in the carboxylic acids to be vinylized.

The process of the invention can be carried out using a homogeneous or heterogeneous catalyst system. A homogeneously catalyzed reaction is preferred, because the high degree of distribution of the catalyst provides better space-time yields than in the case of a heterogeneously catalyzed reaction. Particularly suitable are, therefore, those catalysts that are soluble in the reaction mixture under the conditions of the reaction.

Heterogeneous catalysis is particularly significant in cases in which the ligands are linked to a polymeric, insoluble basic framework.

The success of the process of the invention is not, as far as has as yet been observed, basically dependent on the nature of the carboxylic acid or on the number of carboxyl groups in the starting compound. Monovalent and polyvalent aliphatic, cycloaliphatic, araliphatic, and aromatic carboxylic acids are suitable for this purpose, prime examples being those acids whose vinyl esters are of special significance for the preparation of plastics, such as acetic acid, propionic acid, and adipic acid.

Also, substituted carboxylic acids are equally well suited for use as starting compounds for the process of the invention, if the substituents are inert under the conditions of the reaction. Such inert substituents are alkoxy, aryloxy, halogen, alkoxycarbonyl oder nitrile groups. Monomethyl succinate, monomethyl malonate, monomethyl maleates, chloroacetic acid, and 4-nitrobenzoic acid are examples of such substituted carboxylic acids.

The process of the invention can be carried out in conventional manner, for example as follows:

The carboxylic acid, optionally a solvent, and the catalyst are placed in the reactor, and this mixture is usually first brought to the reaction temperature, gaseous acetylene is added and is replenished at the same rate as it is consumed. As a precautionary measure, the acetylene can be diluted with an inert gas such as helium, methane, propane, argon or, preferably, nitrogen.

The reaction may be carried out in the presence of an organic solvent. Hydrocarbons such as n-pentane, n-hexane are suitable, for example the xylenes, or preferably toluene, in addition ethers, e.g., 1,4-dioxane or ethylene glycol dimethyl ether, or preferably tetrahydrofuran, N,N-dialkylamides, e.g., N-methyl-2-pyrrolidone or N,N-dimethylformamide, as well as carboxylates such as methyl acetate, ethyl acetate, or butyl acetate. In a preferred embodiment, the end product is itself used as solvent.

The acetylene is normally used in a molar ratio of from 1:1 to 100:1 and preferably from 1.2:1 to 30:1 and more preferably from 1.5:1 to 10:1, based on the carboxyl groups to be converted.

The reaction can be carried out without the use of pressure, if desired, but also takes place without problem up to acetylene pressures of 25 bar. To achieve a satisfactory space-time yield, it is preferably carried out under acetylene pressures ranging from 15 to 20 bar.

The temperature of the reaction is from 50° to 200° C. and preferably from 80° to 150° C. A temperature range of from 100° to 120° C. is particularly preferred on account of the good space-time yields achieved accompanied by high product selectivity.

The purification of the reaction mixture is carried out in conventional manner, preferably by fractional distillation or by crystallization. The concentration of by-products ist usually very low and these mainly consist of polymerization products of acetylene. Recovered catalysts, solvents, and unconverted starting compounds are advantageously recycled to the vinylation stage.

It is not normally of any advantage to recycle to the synthesis process the small amounts of acetylene remaining in the autoclave after the reaction has taken place, and the complicated means required for this purpose in other processes is thus not required here.

The vinyl esters prepared in accordance with the process of the invention are suitable as monomers or comonomers for the preparation of polymer dispersions serving, for example, as weather-resistant paints.

EXAMPLES

A mixture of 0.2 mol (ag) of a carboxylic acid, b mmol of catalyst metal (used as salt of a platinum metal or as a finished platinum metal catalyst complex), c mmol of a ligand and 120 g of toluene were subjected to vinylation at 100° C. under a nitrogen pressure of 5 bar and an acetylene pressure of 14 bar. Conventional purification, by distillation, of the reaction mixture provided the vinyl ester of the carboxylic acid in a yield of y %. Details and results of these examples are listed in the table below.

R—CN  (Ia), in which R stands for a $C_1$–$C_4$ alkyl group, a cyclopentyl, cyclohexyl, phenyl, benzyl or 2-phenylethyl group, which radicals can also carry inert substituents.

4. A process as claimed in claim 1, wherein the ligands in the catalyst complexes are tertiary amines of the formula IIa

(IIa)

in which the radicals R can be the same or different and have the meaning stated in claim 3.

5. A process as claimed in claim 1, wherein the ligands in the catalyst complexes are hetero-aromatic nitrogen bases (IIb).

6. A process as claimed in claim 1, wherein the hetero-aromatic nitrogen bases are pyridine or 1,10-phenanthroline.

| Example | Carboxylic Acid | a [g] | Metal | [mmol] | Ligand | [mmol] | Reaction Time [h] | Yield of Vinyl Ester [%] |
|---|---|---|---|---|---|---|---|---|
| 1 | 2-ethylhexanoic acid | 29 | Ru | 2.8 | $NEt_3$ | 6 | 15 | 94 |
| 2 | 2-ethylhexanoic acid | 29 | Ru | 6 | CO[1)] | | 11 | 80 |
| 3 | 2-ethylhexanoic acid | 29 | Ru | 2 | $(n\text{-Bu})_3P$ | 4 | 7 | 75 |
| 4 | 4-tert.-butylbenzoic acid | 36 | Ru | 2.5 | $(n\text{-Bu})_3P$ | 4 | 12 | 89 |
| 5 | suberic acid[2)] | 35 | Ru | 2.5 | $(n\text{-Bu})_3P$ | 4 | 17 | 55 |
| 6 | monomethyl succinate | 26 | Ru | 2.5 | $(n\text{-Bu})_3P$ | 4 | 8 | 74 |
| 7 | 2-ethylhexanoic acid | 29 | Ru | 2.4 | $(MeO)_3P$ | 4 | 5 | 52 |
| 8 | 2-ethylhexanoic acid | 29 | Ru[2)] | | 3) | | 13 | 76 |
| 9 | 2-ethylhexanoic acid | 29 | Ru | 7.4 | 4) | | 17 | 82 |

[1)] as $Ru_3(CO)_{12}$
[2)] solvent: 120 g of tetrahydrofuran
[3)] recovered catalyst from Example 1
[4)] $RuCl_3 \cdot xH_2O$ supported on a polystyrene/divinylbenzene copolymer bearing $(CH_3)_2N$ groups; Ru content 9.4 wt %

We claim:

1. A process for the preparation of vinyl carboxylates by the reaction of a carboxylic acid with acetylene in the presence of a platinum metal complex catalyst, wherein a complex of a platinum metal is used as platinum metal complex catalyst, which contains as ligands carbon monoxide, a monovalent or polyvalent nitrile (I), a monovalent or polyvalent nitrogen base (II), a monovalent or polyvalent tertiary phosphorus compound (III) having C-organic and/or O-organic radicals, or mixtures of said compounds.

2. A process as claimed in claim 1, wherein ruthenium is used as platinum metal.

3. A process as claimed in claim 1, wherein the ligands in the catalyst complexes are nitriles of the formula Ia 7. A process as claimed in claim 1, wherein the ligands in the catalyst complexes are tertiary phosphorus compounds having C-organic and/or O-organic radicals of the formula (III)

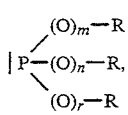
(III)

in which the radicals R can be the same or different, and have the meaning stated in claim 3 and in which m, n and r denote zero or 1.

8. A process as claimed in claim 1, wherein catalyst complexes are used, in which the ligands I to III are linked to a polymer.

* * * * *